US010272292B1

(12) United States Patent
Leu et al.

(10) Patent No.: US 10,272,292 B1
(45) Date of Patent: Apr. 30, 2019

(54) ADAPTIVE SPORT POSTURE SENSING SYSTEM AND METHOD

(71) Applicant: NATIONAL TAIWAN NORMAL UNIVERSITY, Taipei (TW)

(72) Inventors: Yih-Guang Leu, Taipei (TW); Jon-Chao Hong, Taipei (TW)

(73) Assignee: NATIONAL TAIWAN NORMAL UNIVERSITY (TW)

( * ) Notice: Subject to any disclaimer, the term of this patent is extended or adjusted under 35 U.S.C. 154(b) by 0 days.

(21) Appl. No.: 16/114,349

(22) Filed: Aug. 28, 2018

(30) Foreign Application Priority Data

May 14, 2018 (TW) .............................. 107116341 A (51) Int. Cl.
G08B 23/00 (2006.01)
A63B 24/00 (2006.01)
A63B 71/06 (2006.01)

(52) U.S. Cl.
CPC ...... *A63B 24/0006* (2013.01); *A63B 24/0062* (2013.01); *A63B 71/0622* (2013.01); *A63B 2024/0012* (2013.01); *A63B 2220/803* (2013.01); *A63B 2220/836* (2013.01); *A63B 2230/62* (2013.01)

(58) Field of Classification Search
None
See application file for complete search history.

(56) References Cited

U.S. PATENT DOCUMENTS

| | | | | |
|---|---|---|---|---|
| 7,602,301 B1* | 10/2009 | Stirling | ................ | A61B 5/1127 340/573.1 |
| 10,065,074 B1* | 9/2018 | Hoang | ............... | A63B 24/0003 |
| 2003/0134724 A1* | 7/2003 | Tuttle | ................... | A63B 21/065 482/105 |
| 2008/0295216 A1* | 12/2008 | Nordstrom | ......... | A41D 13/0015 2/69 |
| 2008/0295230 A1* | 12/2008 | Wright | ............... | A41D 13/0015 2/455 |
| 2013/0326785 A1* | 12/2013 | Cornacchiari | ........... | A41D 1/00 2/69 |
| 2015/0366504 A1* | 12/2015 | Connor | ................ | A61B 5/6804 600/301 |
| 2016/0029929 A1* | 2/2016 | Worthen | ............... | A61B 5/1116 600/595 |
| 2016/0316825 A1* | 11/2016 | Cutler | .................... | A41D 1/084 |
| 2018/0008169 A1 | 1/2018 | Chang | | |
| 2018/0200572 A1* | 7/2018 | Wagner | .............. | A63B 23/0233 |

FOREIGN PATENT DOCUMENTS

TW        I491379 B        7/2015

* cited by examiner

*Primary Examiner* — Julie B Lieu
(74) *Attorney, Agent, or Firm* — Schmeiser, Olsen & Watts, LLP (57) ABSTRACT

An adaptive sport posture sensing system has a sensing device, a sensing signal acquiring unit and a sport posture processing unit. In the determination mode, the sport posture processing unit selects one piece among multiple established pieces of sport posture reference data according to a sport name, a wearing position and one piece of user body information, the sensing signal acquiring unit obtains at least one first sensing signal sensed by the sensing device, and the sport posture processing unit compares a sport posture data generated based upon the at least one first sensing signal with the selected piece of the sport posture reference data, so as to determine whether a sport posture of the user is correct or not.

13 Claims, 6 Drawing Sheets

ADAPTIVE SPORT POSTURE SENSING SYSTEM AND METHOD

CROSS-REFERENCE TO RELATED APPLICATION

This non-provisional application claims priority under 35 U.S.C. § 119(a) on Patent Application No(s). 107116341 filed in Taiwan, R.O.C. on May 14, 2018, the entire contents of which are hereby incorporated by reference.

TECHNICAL FIELD

The present disclosure relates to a sport posture sensing technology, in particular, to an adaptive sport posture sensing system and method, which are not affected by different wearing positions, different wearing manners, heights, genders, ages and health statuses of different users.

RELATED ART

The current market has a plurality of wearable devices being sold, and the partial wearable device can sense sport postures of users. By sensing the sport posture of a user, the wearable device (or the computing device communicatively linked to the wearable device) can determine whether the sport posture of the user is correct or not, such that the body status or the sport status of the user can be further evaluated. However, the wearing position and the wearing manner of the conventional wearable device are fixed. For example, when the wearable device which should be worn on the wrist is worn on the shank of the user, the wearable device cannot correctly determine the sport posture of the user.

In short, the user must wear the conventional wearable device on the correct wearing position and in the correct wearing manner to allow the wearable device to correctly determine whether the sport posture of the user is correct or not. That is, the conventional wearable device has no adaptivity. Thus, the user must buy wearable devices for different wearing positions, and it incurs high acquisition costs.

For example, TW Patent 1491379 provides a wearable motion sensing device worn on the limbs of the user, so as to detect the physiological motion signal of the limbs of the user. The wearable motion sensing device comprises a sensing module, a transmission module and a stabilization module, and is dedicated to the application of joint bending posture correction or rehabilitation. The wearable motion sensing device provided by TW Patent 1491379 should be worn on the limbs of the user, and it has no adaptivity design for arbitrary wearing position and arbitrary wearing manner.

For another example, TW Patent M537280 provides a fall detection system comprising a wearable device and a processor, and the wearable device is configured to be worn by a user. The wearable device is installed with inertia sensors for detecting sport posture data of the user. TW Patent M537280 mainly utilizes the wearable device to detect normal sport posture data and stores the normal port posture data in a database as a reference data, wherein new sport posture data can be compared with the reference data to judge whether the new sport posture data is an abnormal data for achieving the objective of fall detection. It is noted that, TW Patent M537280 neither discloses the adaptivity design for arbitrary wearing position and arbitrary wearing manner.

In addition, the detected posture signals or physiological signals may have large differences since users have different heights, different weights, different ages, different genders and different health statuses. Therefore, the conventional technology determines whether the sport posture of the user is correct or not without considering the height, the weight, the age, the gender and the health status of user.

SUMMARY

Accordingly, to cure deficiency of the conventional technology, an embodiment of the present disclosure provides an adaptive sport posture sensing system and an adaptive sport posture sensing method, which allow the user to wear the sensing device of the adaptive sport posture sensing system on arbitrary wearing position and in arbitrary wearing manner, and still can correctly determine a sport posture of the user. In addition, the adaptive sport posture sensing system and method further consider a height, a weight, an age, a gender and a health status of the user to determine the sport posture of the user. Therefore, the determination precision for the sport posture of the present disclosure is more accurate than that of the conventional wearable device. In short, the adaptive sport posture sensing system and method have the adaptivity design for arbitrary wearing position, arbitrary wearing manner and arbitrary user.

According to objective of the present disclosure, an adaptive sport posture sensing system is provided, comprising: a first sensing device, comprising at least one first sensor, configured to be worn by a first user; a first sensing signal acquiring unit, electrically connected or communicatively linked to the first sensing device; and a sport posture processing unit, electrically connected or communicatively linked to the first sensing signal acquiring unit; wherein in a determination mode, the sport posture processing unit selects a first piece among multiple established batches of sport posture reference data according to a first sport name, a first wearing position and first user body information, the first sensing signal acquiring unit obtains at least one first sensing signal sensed by the first sensing device, and the sport posture processing unit compares first sport posture data generated based upon the at least one first sensing signal with the selected first piece of the sport posture reference data, so as to determine whether a first sport posture of the first user is correct or not.

Optionally, in the embodiment of the present disclosure, the adaptive sport posture sensing system further comprises: a second sensing device, comprising at least one second sensor, being configured to be worn by a second user; and a second sensing signal acquiring unit, electrically connected or communicatively linked to the second sensing device and the sport posture processing unit; wherein in the determination mode, the sport posture processing unit selects a second piece among the established pieces of the sport posture reference data according to a second sport name, a second wearing position and second user body information, the sensing signal acquiring unit obtains at least one second sensing signal sensed by the second sensing device, and the sport posture processing unit compares second sport posture data generated based upon the at least one second sensing signal with the selected second piece of the sport posture reference data, so as to determine whether a second sport posture of the second user is correct or not.

Optionally, in the embodiment of the present disclosure, the sport posture processing unit comprises: two client-side processing units, electrically connected or communicatively linked to the first sensing signal acquiring unit and second sensing signal acquiring unit, respectively; and a server-side processing unit, electrically connected or communicatively linked to the two client-side processing units.

Optionally, in the embodiment of the present disclosure, in a learning mode, the sport posture processing unit records the first sport name, the first wearing position and the first user body information, the first sensing signal acquiring unit obtains at least one training signal sensed by the first sensing device, and the sport posture processing unit, according to the at least one training signal, establishes the first piece of the sport posture reference data corresponding to the first sport name, the first waring position and the first user body information.

Optionally, in the embodiment of the present disclosure, the first piece of the sport posture reference data is further selected according to a wearing manner.

Optionally, in the embodiment of the present disclosure, the first user body information comprises a height, a weight, a gender, an age and a health status of the first user.

Optionally, in the embodiment of the present disclosure, the sport posture processing unit further comprises an audio input unit, and the first user controls the adaptive sport posture sensing system via the audio input unit.

Optionally, in the embodiment of the present disclosure, the at least one first sensor comprises a 9-axis sensor, a pressure sensor, a tension sensor, a temperature sensor or a vibration sensor.

According to objective of the present disclosure, an adaptive sport posture sensing method is provided, comprising: in a determination mode: selecting a first piece among multiple established pieces of sport posture reference data according to a first sport name, a first wearing position and first user body information; obtaining at least one first sensing signal sensed by a first sensing device worn by a first user; and comparing first sport posture data generated based upon the at least one first sensing signal with the selected first piece of the sport posture reference data, so as to determine whether a first sport posture of the first user is correct or not.

Optionally, in the embodiment of the present disclosure, the adaptive sport posture sensing method further comprises: in a learning mode: recording the first sport name, the first wearing position and the first user body information; obtaining at least one training signal sensed by the first sensing device; and establishing, according to the at least one training signal, the first piece of the sport posture reference data corresponding to the first sport name, the first waring position and the first user body information.

To sum up, the adaptive sport posture sensing system and method of the present disclosure can allow the user to wear the sensing device on arbitrary wearing position and in arbitrary wearing manner. In the learning mode, the adaptive sport posture sensing system and method can establish multiple pieces of sport posture reference data corresponding to wearing manners, wearing positions and pieces of user body information, such that in the determination mode, one piece of the sport posture reference data is selected as a reference standard for determining whether the sport posture of the user is correct or not. Thus, the adaptive sport posture sensing system and method do not limit the wearing position, the wearing manner of the sensing device as well as the wearing person (i.e. being adaptive to different users), and the usage convenience and flexibility of the user can be enhanced. In addition, the adaptive sport posture sensing system and method of the present disclosure is not only applied for determination of sport posture of exercising, but also applied for determination of sport posture of fitness, gaming, medical treatment or rehabilitation, thus making the present disclosure have a potential for production.

BRIEF DESCRIPTION OF THE DRAWINGS

In order that the present disclosure may be better understood and readily carried into effect, certain embodiments of the present disclosure will now be described with reference to the accompanying drawings, wherein.

DETAILED DESCRIPTION OF THE PREFERRED EMBODIMENTS

To fully understand the purpose, features, and effects of the present disclosure, the present disclosure will be described in detail by the following specific examples and in conjunction with the accompanying drawings.

Embodiments of the present disclosure provide an adaptive sport posture sensing system and method, which allow the user to flexibly determine a wearing position and a wearing manner of the sensing device, and the adaptive sport posture sensing system and method do not wrongly detect the sport posture of the user due to different wearing positions, different wearing manners and user body differences. Further, the adaptive sport posture sensing system and method have two modes, namely a learning mode and a determination mode.

In the learning mode, the adaptive sport posture sensing system and method record a wearing position and a wearing manner of a sensing device (in another embodiment, merely the wearing position is recorded without considering the wearing manner) and user body information, wherein the user body information comprises a height, a weight, an age, a health status and a gender of a user. In the learning mode, for each sport, the adaptive sport posture sensing system and method obtains training signals (sensed by the sensing device worn by the user) associated with the correct sport posture of the user, and uses the learning algorithm (such as, deep learning algorithm with neural network architecture, but the present disclosure is not limited thereto) to establish one piece of sport posture reference data according to the above training signals sensed by the sensing device worn by the user.

In a determination mode, the adaptive sport posture sensing system and method obtain the wearing position, the wearing manner, the user body information and the sport name, which are input by the user, and then select one piece among the multiple established pieces of the sport posture reference data accordingly. Then, the adaptive sport posture sensing system and method in the determination mode receive sport posture data generated by multiple sensing signals being generated by sensing the sport posture of the user. Next, the adaptive sport posture sensing system and method in the determination mode determines whether the sport posture of the user is correct or not according to the sport posture data and the selected piece of the sport posture reference data.

In short, the adaptive sport posture sensing system and method have a learning mode and a determination mode. In the learning mode, by obtaining the training signals, for each sport corresponding to the sport name, each piece of the sport posture reference data corresponding to the wearing position, the wearing manner and the user body information is established. In the determination mode, for the sport corresponding to the sport name, the piece of the sport posture reference data corresponding to the wearing position, the wearing manner and the user body information is selected, and the sport posture data of the user generated by multiple sensing signals is compared with the selected piece of the sport posture reference data, so as to determine whether the sport posture data of the user corresponding to the sport is correct or not.

After illustrating the main concept and the rough implementation of the present disclosure, embodiments accompanying with drawings of the present disclosure are described to illustrate at least one implementation of the present disclosure.

Figure 1:
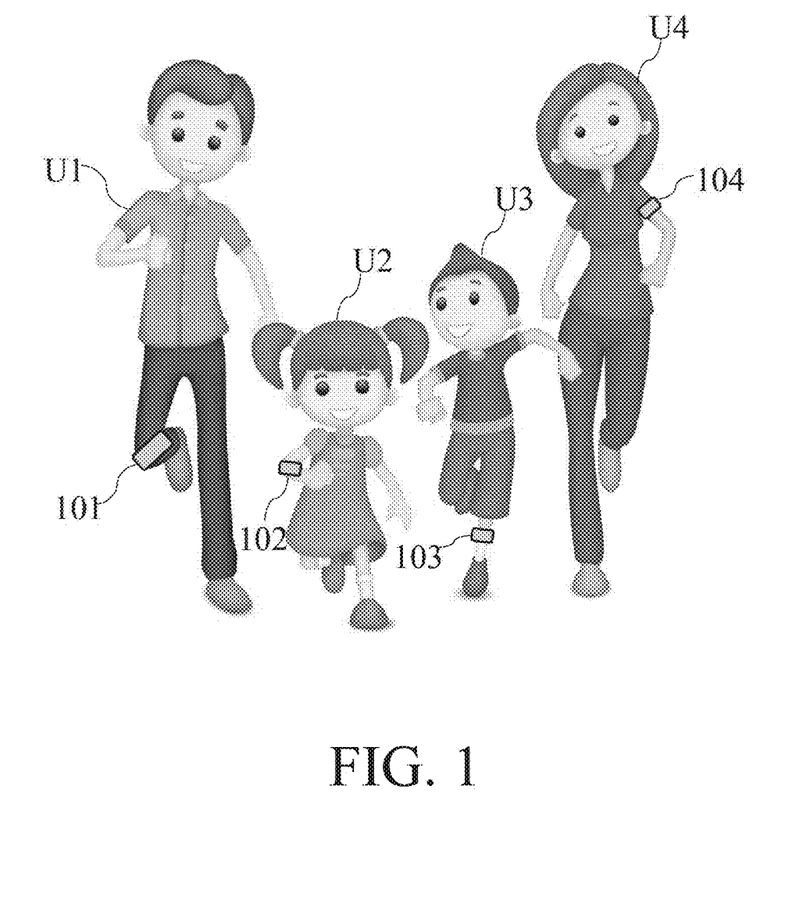
FIG. 1 is a schematic diagram showing that sensing devices of an adaptive sport posture sensing system provided by an embodiment of the present disclosure are worn on different wearing positions of users.

Firstly, referring to FIG. 1, FIG. 1 is a schematic diagram showing that sensing devices of an adaptive sport posture sensing system provided by an embodiment of the present disclosure are worn on different wearing positions of users. FIG. 1 illustrates a case that members of a family jog, and the members of the family comprises users U1 through U4. The user body statues (i.e. presented by different pieces of user body information) of the users U1 through U4 are different, and thus the sensing devices 101 through 104 in the adaptive sport posture sensing system may be worn by the users U1 through U4 on different wearing positions and in different wearing manners. For example, the user U1 is a physically fit man with a good health status, and thus the sensing device 101 may be bound to the right knee of the user U1; the user U2 is a slim girl with a poor health status, thus it is hard to bind the sensing device 102 to the knee of the user U2, and the sensing device 102 can be attached on the right forearm of the user U2; the user U3 is a physically fit man with a good health status, and thus the sensing device 103 may be bound to the left knee of the user U3; and the user U4 is a slim woman with a good health status, thus it is hard to bind the sensing device 104 to the knee of the user U4, and the sensing device 104 can be bound to the left upper arm of the user U4.

In the embodiment of FIG. 1, the adaptive sport posture sensing system comprises sensing devices 101 through 104, sensing signal acquiring units and a sport posture processing unit, wherein each of the sensing devices 101 through 104 comprises at least one sensor for sensing the users U1 through U4 exercising. The sensing signal acquiring unit and the sensing device can be integrated into a wearable device, and the sport posture processing unit can be implemented by one or more processing units and input/output circuits of the wearable devices, or alternatively, the sport posture processing unit can be implemented by a server or computing device communicatively linked to the wearable devices.

Take jog postures as an example, the sport posture processing unit of the adaptive sport posture sensing system in the learning mode can record the wearing positions, the wearing manners and the pieces of the user body information of the users U1 through U4, and the sensing signal acquiring units can obtain the training signals which the sensing devices 101 through 104 respectively sense the jog postures of the users U1 through U4. Thus, the multiple pieces of the sport posture reference data of the jog, which are corresponding to the users U1 through U4, can be established. Next, in the determination mode, the sensing signal acquiring units of the adaptive sport posture sensing system obtain sensing signals which the sensing devices 101 through 104 sense the jog postures of the users U1 through U4, and then the sport posture processing unit generates multiple pieces of the sport posture data correspondingly, and compares the multiple pieces of the sport posture data of the users U1 through U4 with the selected multiple pieces of the sport posture reference data associated with the users U1 through U4, so as to determine whether the jog postures of the user U1 through U4 are correct or not.

In short, being not like the conventional sensing device which must be worn on the specific wearing position and in the specific wearing manner, the adaptive sport posture sensing systems has the adaptivity which the sensing devices 101 through 104 can be worn on arbitrary wearing position and in arbitrary wearing manner, and the adaptive sport posture sensing system can further considers the user body statuses of the users U1 through U4 (p.s. presented by the multiple pieces of the user body information of the users U1 through U4) to determine whether the sport postures of the user U1 through U4 are correct or not. Generally, for the same sport, the sensing signals of different users U1 through U4 are not only affected by the wearing manners and the wearing positions, but also affected by the body types, harmonicities and explosive forces exerted by the users U1 through U4. Since the adaptive sport posture sensing system according to the embodiment of the present disclosure considers the user body statuses of the users U1 through U4, the precision for determining the sport postures of the users U1 through U4 is further enhanced.

Figure 2:
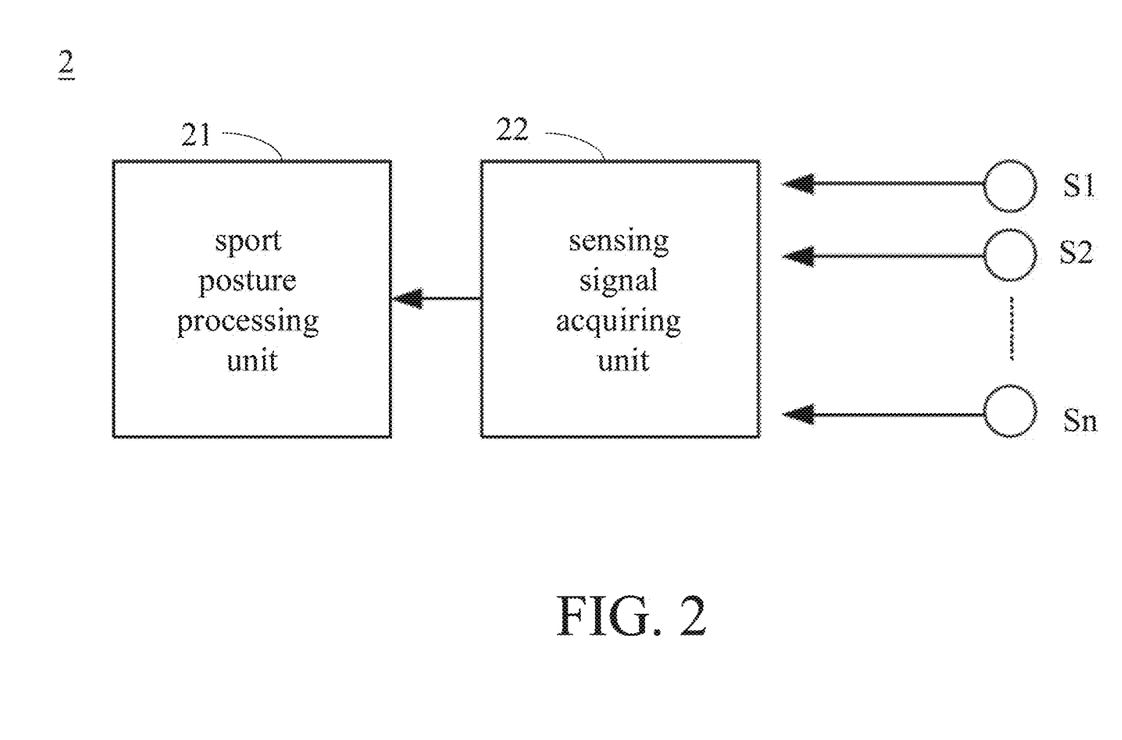
FIG. 2 is a block diagram of an adaptive sport posture sensing system according to an embodiment of the present disclosure.

Next, further referring to FIG. 2, FIG. 2 is a block diagram of an adaptive sport posture sensing system according to an embodiment of the present disclosure. The adaptive sport posture sensing system 2 comprises a sport posture processing unit 21, a sensing signal acquiring unit 22 and a sensing device formed by sensors S1 through Sn, wherein the sensors S1 through Sn are electrically connected or communicatively linked to the sensing signal acquiring unit 22, and the sensing signal acquiring unit 22 is electrically connected or communicatively linked to the sport posture processing unit 21. In the embodiment, the sport posture processing unit 21, the sensing signal acquiring unit 22 and the sensors S1 through Sn can be integrated into a single one wearable device; or alternatively, merely the sensors S1 through Sn and the sensing signal acquiring unit 22 can be integrated into the single one wearable device, and the sport posture processing unit 21 is for example a server or a computing device, such as a computer, a pad or a smart phone.

Each of the sensors S1 through Sn is one or combination of a 9-axis sensors (i.e. comprising a 3-axis magnetic sensor, a 3-axis accelerometer and a 3-axis gyro), a pressure sensor, a tension sensor, a temperature sensor and a vibration sensor, which is used to sense the sport posture of the user to generate the sensing signals (in the determination mode) or the training signals (in the learning mode). The sensing signal acquiring unit 22 is used to obtain the sensing signals or the training signals which the sensors S1 through Sn sense the sport posture of the user in the determination mode or the learning mode, and to transmit the obtained sensing signals or training signals to the sport posture processing unit 21. The sport posture processing unit 21 in the learning mode is used to establish the multiple pieces of the sport posture reference data of each sport associated with the wearing manners, the wearing positions and the pieces of the user body information according to the training signals; in the determination mode, the sport posture processing unit 21 selects one piece among the multiple established pieces of the sport posture reference data associated with the sport according to the wearing manner, the wearing position and the user body information of the user, and the sport posture processing unit 21 compares the sport posture data generated by the sensing signals with the selected piece of the sport posture reference data, so as to determine whether the sport posture of the user is correct or not.

The establishment of the multiple pieces of the sport posture reference data in the learning mode can be implemented by using the learning algorithm, such as an artificial intelligence learning algorithm or a statistical learning algorithm associated, the present disclosure is not limited thereto, and one of other algorithms may be used for learning, such as the data mining algorithm, the fuzzy control algorithm, the neural network algorithm or the deep learning algorithm. In addition, each piece of the sport posture reference data has information of the corresponding wearing manner, the corresponding wearing position, the corresponding user body information and the corresponding sport name. Thus, for different users, different wearing manners and different wearing positions, the adaptive sport posture sensing system can still accurately determine the sport posture of the user. Since the adaptive sport posture sensing system provides the great adaptivity, the user can buy merely one wearable device rather than multiple wearable devices, and the merely one wearable device can be worn by the different users on different wearing positions and in different wearing manners due to its adaptivity. Therefore, the present disclosure can reduce the acquisition costs of the wearable devices.

Specifically, the sport posture processing unit 21 uses the sensing signal merging and filtering technology, user inputs (comprising the sport name (or the decomposed posture name), the user body information, the wearing manner, the wearing position and the mode selection (the entrance of the learning mode of the determination mode)) and the learning algorithm to carry out the functions of the sport posture learning, the sport posture determination, the user identification and the sport posture determination result outputting. It is noted that, the sport posture processing unit 21 can have an audio input unit, such that the user can input the sport name, the decomposed posture name and the posture sequence when exercising, so as to improve the learning efficiency of the adaptive sport posture sensing system.

The adaptive sport posture sensing system in FIG. 2 for example is suitable for the personal sport or the fitness, and the user can define the sport posture, and use the adaptive sport posture sensing system to evaluate the efficiency of the sport or the fitness. For example, in the learning mode, the user can input the wearing manner and the wearing position to indicate that the sensing device is bound on the abdomen, and input the sport name of sit-up, and the user can further use the audio input to make the sport posture processing unit 21 obtain the training signals (sensed by the sensing device) of the sit and up postures associated with the sit-up, so as to establish the piece of the sport posture reference data of the sit-up. Then, in the determination mode, the sport posture processing unit 21 determines whether the sport posture of the sit-up exercised by the user is correct or not according to the sport posture data and the selected piece of the sport posture reference data, wherein the sport posture data is generated according to the obtained sensing signals.

Furthermore, the sport posture processing unit 21 can be extended to wirelessly or wiredly linked to the remote or cloud server, the database or the cloud computing device, so as to achieve the learning of the multiple sport postures of the users, the determination of the multiple sport postures of the users, the multi-user identification and the multi-determination outputting of the multiple sport postures of the users. The details can be illustrated in the embodiments of FIG. 3 and FIG. 4 as follows.

Figure 3:
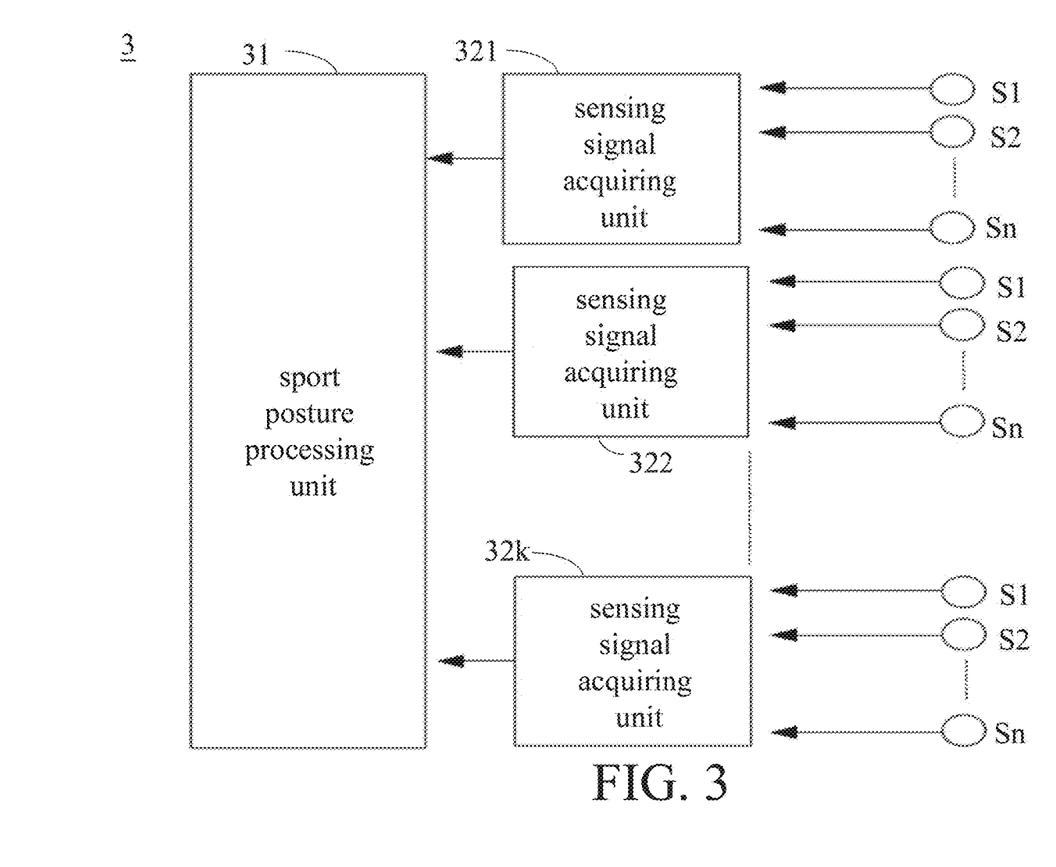
FIG. 3 is block diagram of an adaptive sport posture sensing system according to another embodiment of the present disclosure.

Next, referring to FIG. 3, FIG. 3 is block diagram of an adaptive sport posture sensing system according to another embodiment of the present disclosure. The adaptive sport posture sensing system 3 comprises a sport posture processing unit 31, sensing signal acquiring units $32l$ through $32k$ and sensing devices, wherein each of the sensing devices is formed by sensors S1 through Sn, the sensing devices are respectively electrically connected or communicatively linked to the sensing signal acquiring units $32l$ through $32k$, and the sensing signal acquiring units $32l$ through $32k$ are electrically connected or communicatively linked to the sport posture processing unit 31.

It is noted that, though the number of the sensors of each sensing device is n, the present disclosure is not limited thereto. The numbers of the sensors of different sensing devices may be not identical. Further, in the embodiment, each of the sensing devices and the corresponding one of the sensing signal acquiring units $32l$ through $32k$ are integrated into a single one wearable device, and in the embodiments, k wearable devices are provided to and worn by the k users. The sport posture processing unit 31 can be a server or a computing device, such as a computer, a pad or a smart phone, or alternatively integrated into one of the k wearable devices.

In the embodiment, the adaptive sport posture sensing system 3 is suitable for sport teaching or fitness teaching, such as Tai Chi, martial arts or Tae Kwon Do teaching. By the group (or remote) teaching, one user (for example, the coach) in the group can demonstrate one sport posture to establish the piece of the sport posture reference data, and other users (for example, students) in the group can follow the demonstrated one sport posture to exercise. Next, the sport posture processing unit 31 can compare the piece of the sport posture reference data with the multiple pieces of the sport posture data of the other users to determine whether the sport postures of the other users are correct or not, so as to evaluate the sport and learning effectiveness.

Figure 4:
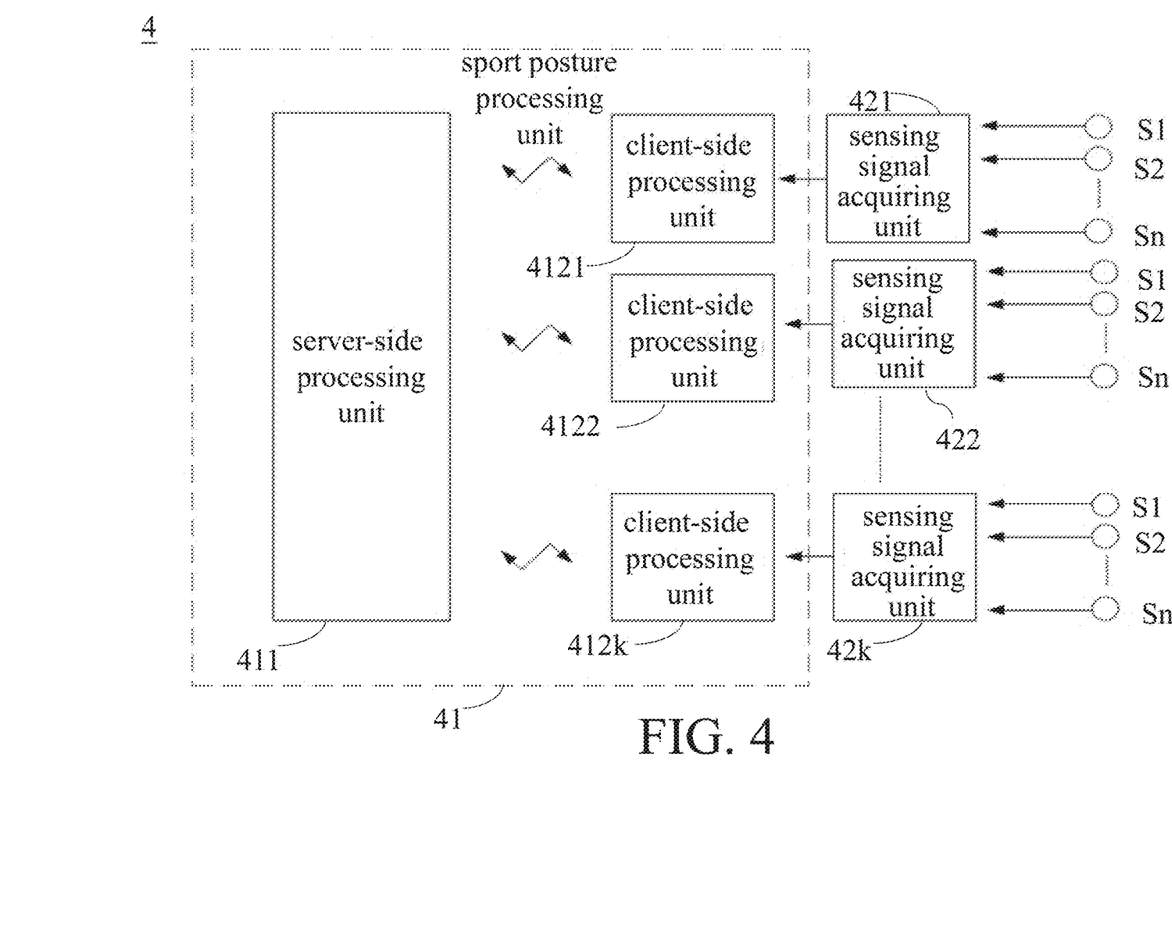
FIG. 4 is block diagram of an adaptive sport posture sensing system according to another embodiment of the present disclosure.

Next, referring to FIG. 4, FIG. 4 is block diagram of an adaptive sport posture sensing system according to another embodiment of the present disclosure. The adaptive sport posture sensing system 4 comprises a sport posture processing unit 41, sensing signal acquiring units $42l$ through $42k$ and sensing devices, wherein each of the sensing devices is formed by sensors S1 through Sn, the sensing devices are respectively electrically connected or communicatively linked to the sensing signal acquiring units $42l$ through $42k$, and the sensing signal acquiring units $42l$ through $42k$ are electrically connected or communicatively linked to the sport posture processing unit 41.

It is noted that, though the number of the sensors of each sensing device is n, the present disclosure is not limited thereto. The numbers of the sensors of different sensing devices may be not identical. In addition, the sport posture processing unit 41 can be formed by a server-side processing unit 411 and client-side processing units 412l through 412k, wherein client-side processing units 412l through 412k, wherein the client-side processing units 412l through 412k are communicatively linked to the server side processing unit 411. In the embodiment, each of the sensing devices and the corresponding one of the sensing signal acquiring units 42l through 42k are integrated into a single one wearable device, and thus k wearable devices are provided to and worn by the k users.

In the embodiment, the adaptive sport posture sensing system 4 can be applied to the sport game (such as, the fitness sport posture of the sit-up, the push-up or the interactive jump, or the sport posture defined in the game), and by the group teaching (i.e. remote teaching), one user of the group demonstrates one sport posture to establish the piece of the sport posture reference data, and other users of the group can exercise according to the demonstrated sport posture for gaming. Next, the sport posture processing unit 41 compares the piece of the sport posture reference data with the multiple pieces of the sport posture data of the other users to determine whether the sport postures of the other users are correct or not, so as to evaluate the gaming scores.

It is noted that, the sport posture processing units 21, 31 and 41 in the adaptive sport posture sensing systems 2, 3 and 4 select corresponding one piece of the sport posture reference data according to the user input user body information, wearing manner, wearing position and the sport name. However, present disclosure is not limited, since the artificial intelligence algorithm has developed more completely, the sport posture processing units 21, 31 and 41 can further recommend one possible piece of the sport posture reference data to the user according to the obtained sport posture data, and the user can confirm whether the possible piece of the sport posture reference data is correct or not.

Figure 5:
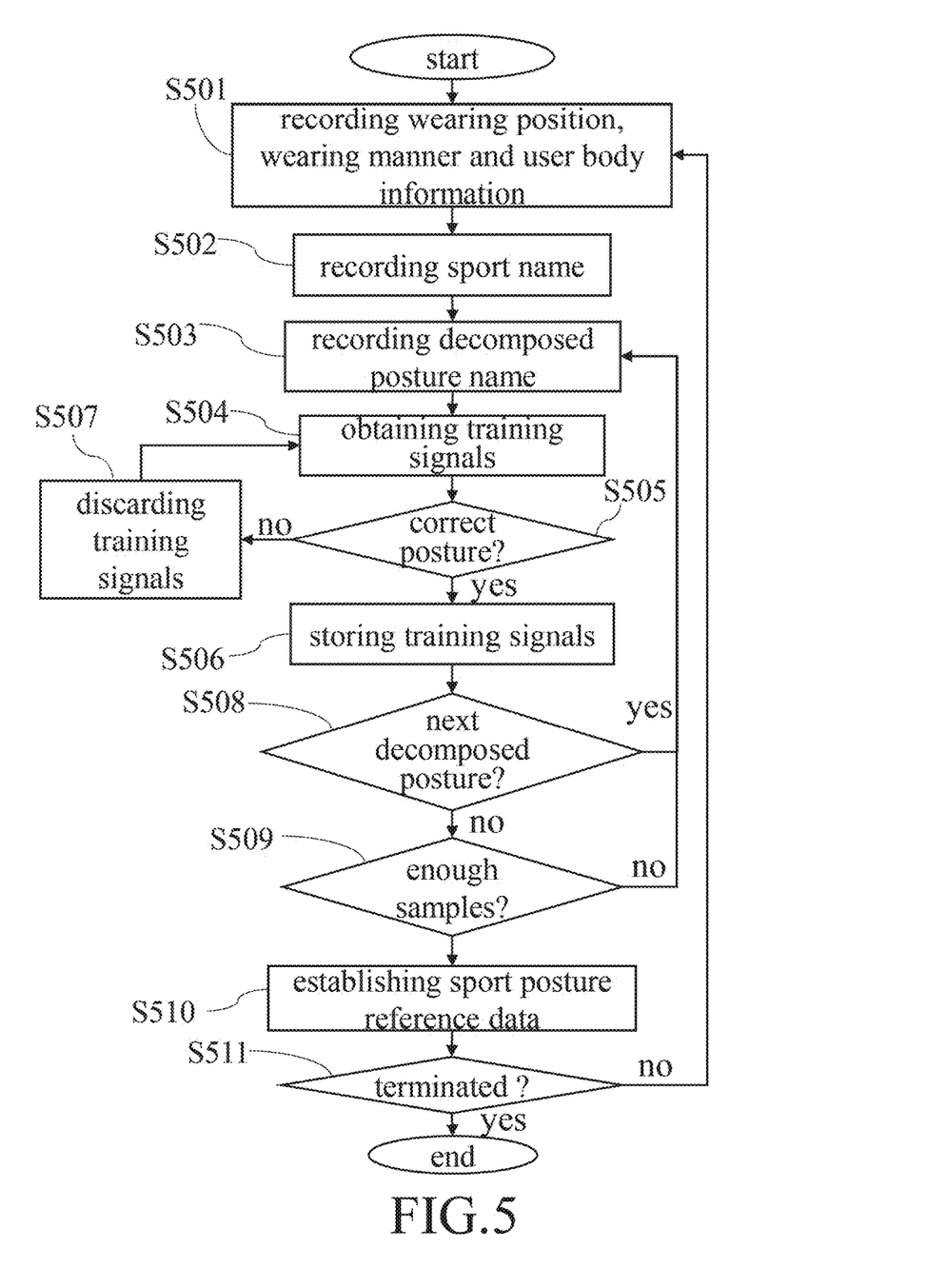
FIG. 5 is a flow chart of steps executed in a learning mode associated with the adaptive sport posture sensing system or method according to an embodiment of the present disclosure.

Next, referring to FIG. 5, FIG. 5 is a flow chart of steps executed in a learning mode associated with the adaptive sport posture sensing system or method according to an embodiment of the present disclosure. Firstly, at step S501, the sport posture processing unit records the wearing manner, the wearing position and the user body information. Then, at step S502, the sport posture processing unit records the sport name of the sport to be learned, such as the push-up. Next, at step S503, the sport posture processing unit records the decomposed posture name, for example, the up or down of the push-up. Next, at step S504, the sport posture processing unit obtains the training signals (sensed by the sensing device) corresponding to the decomposed posture. Next, at step S505, the sport posture processing unit determines whether the training signals corresponding to the decomposed posture are correct or not according to the user input confirmation. If the training signals corresponding to the decomposed posture are not correct, the sport posture processing unit discards the training signals corresponding to the decomposed posture at step S507, and then step S505 is executed again. If the training signals corresponding to the decomposed posture are correct, the sport posture processing unit stores the training signals corresponding to the decomposed posture at step S506.

Next, at step S508, the sport posture processing unit confirms whether a next decomposed posture exists according to the user input. If the next decomposed posture exists, step S503 is executed; if the next decomposed posture does not exist, step S509 is executed. For example, the push-up may have two decomposed postures, and the training signals corresponding to two decomposed postures (i.e. the up and down postures) are required to present the whole push-up.

Next, at step S509, the sport posture processing unit determines whether a sample number of the obtained training signals is enough. If the sample number of the obtained training signals is not enough, steps S503 is executed again; if the sample number of the obtained training signals is enough, step S510 is executed. For example, if the sample number of the obtained training signals is 10, the sport posture processing unit can obtain 10 sets of the training signals corresponding to two decomposed postures (i.e. the up and down postures of the push-up). Next, at step S510, the sport posture processing unit establishes the piece of the sport posture reference data corresponding to the user according to the sets of training signals of the sport posture.

At step S511, the sport posture processing unit determines whether the learning mode is terminated according to the user confirmation. If the learning mode is determined to be terminated, all steps of FIG. 5 are terminated; if other pieces of the sport posture reference data should be established, the learning mode is not determined to be terminated, and step S501 is executed. By executing steps of FIG. 5, the multiple pieces of the sport posture reference data corresponding to different sports, different wearing manners, different wearing positions and different user body information can be established. For example, the piece of the sport posture reference data which one user binds the sensing device on his/her waist and exercises the push-up can be established, and another piece of the sport posture reference data which another user attaches the sensing device on his/her arm and exercises the sit-up can be established.

Figure 6:
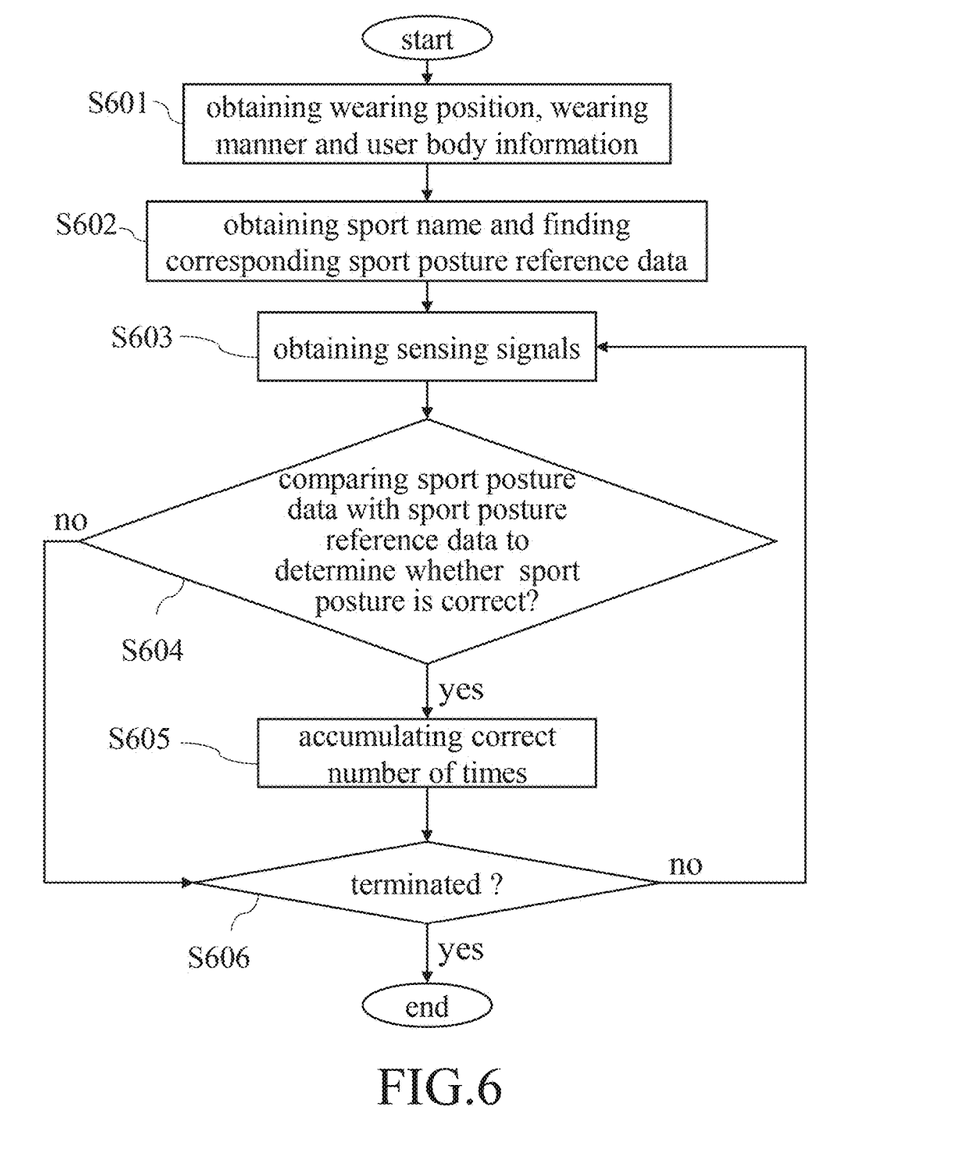
FIG. 6 is a flow chart of steps executed in a determination mode associated with the adaptive sport posture sensing system or method according to an embodiment of the present disclosure.

Next. Referring to FIG. 6, FIG. 6 is a flow chart of steps executed in a determination mode associated with the adaptive sport posture sensing system or method according to an embodiment of the present disclosure. At step S601, the sport posture processing unit obtains the wearing manner, the wearing position and the user body information. At step S602, the sport posture processing unit obtains the sport name, and selects one piece of the sport posture reference data according to the sport name, the wearing manner, the wearing position and the user body information.

Next, at step S603, the sport posture processing unit obtains the sensing signals. Next, at step S604, the sport posture processing unit compares the sport posture data which is generated according to the sensing signals with the selected piece of the sport posture reference data, so as to determine whether the sport posture of the user is correct or not. If the sport posture of the user is correct, a correct number of times is increased; if the sport posture of the user is not correct, step S606 is executed. At step S606, the sport posture processing unit determines whether the determination mode is terminated according to the user confirmation. If the determination mode is determined to be terminated, all steps of FIG. 6 are terminated; if whether a next sport posture is correct or not should be determined, the determination mode is not determined to be terminated, and step S603 is executed. It is noted that the steps of FIG. 6 are not used to limit the present disclosure, and under the case that the determination mode is not terminated, and the sport name, the wearing manner, the wearing position and user body information should be modified, more deciding steps can be added and designed in FIG. 6, such that the user can change and select the next piece of the sport posture reference data as the comparison reference in the determination mode.

Accordingly, by using the adaptive sport posture sensing system and method of the present disclosure, the user can wear the sensing device on arbitrary wearing position of the body and in arbitrary wearing manner. Furthermore, the same sensing device can have the adaptivity for different users. In short, the adaptive sport posture sensing system and method of the present disclosure can enhance the usage convenience and usage flexibility of the sensing device.

While the present disclosure has been described by means of specific embodiments, numerous modifications and variations could be made thereto by those skilled in the art without departing from the scope and spirit of the present disclosure set forth in the claims.

What is claimed is:

1. An adaptive sport posture sensing system, comprising:
   a first sensing device, comprising at least one first sensor, configured to be worn by a first user;
   a first sensing signal acquiring unit, electrically connected or communicatively linked to the first sensing device; and
   a sport posture processing unit, electrically connected or communicatively linked to the first sensing signal acquiring unit;
   wherein in a determination mode, the sport posture processing unit selects a first piece among multiple established batches of sport posture reference data according to a first sport name, a first wearing position and first user body information, the first sensing signal acquiring unit obtains at least one first sensing signal sensed by the first sensing device, and the sport posture processing unit compares first sport posture data generated based upon the at least one first sensing signal with the selected first piece of the sport posture reference data, so as to determine whether a first sport posture of the first user is correct or not.

2. The adaptive sport posture sensing system according to claim 1, further comprising:
   a second sensing device, comprising at least one second sensor, being configured to be worn by a second user; and
   a second sensing signal acquiring unit, electrically connected or communicatively linked to the second sensing device and the sport posture processing unit;
   wherein in the determination mode, the sport posture processing unit selects a second piece among the established pieces of the sport posture reference data according to a second sport name, a second wearing position and second user body information, the sensing signal acquiring unit obtains at least one second sensing signal sensed by the second sensing device, and the sport posture processing unit compares second sport posture data generated based upon the at least one second sensing signal with the selected second piece of the sport posture reference data, so as to determine whether a second sport posture of the second user is correct or not.

3. The adaptive sport posture sensing system according to claim 2, wherein the sport posture processing unit comprises:
   two client-side processing units, electrically connected or communicatively linked to the first sensing signal acquiring unit and second sensing signal acquiring unit, respectively; and
   a server-side processing unit, electrically connected or communicatively linked to the two client-side processing units.

4. The adaptive sport posture sensing system according to claim 1, wherein in a learning mode, the sport posture processing unit records the first sport name, the first wearing position and the first user body information, the first sensing signal acquiring unit obtains at least one training signal sensed by the first sensing device, and the sport posture processing unit, according to the at least one training signal, establishes the first piece of the sport posture reference data corresponding to the first sport name, the first waring position and the first user body information.

5. The adaptive sport posture sensing system according to claim 1, wherein the first piece of the sport posture reference data is further selected according to a wearing manner.

6. The adaptive sport posture sensing system according to claim 1, wherein the first user body information comprises a height, a weight, a gender, an age and a health status of the first user.

7. The adaptive sport posture sensing system according to claim 1, wherein the sport posture processing unit further comprises an audio input unit, and the first user controls the adaptive sport posture sensing system via the audio input unit.

8. The adaptive sport posture sensing system according to claim 1, wherein the at least one first sensor comprises a 9-axis sensor, a pressure sensor, a tension sensor, a temperature sensor or a vibration sensor.

9. An adaptive sport posture sensing method, comprising, in a determination mode, the steps of:
   selecting a first piece among multiple established pieces of sport posture reference data according to a first sport name, a first wearing position and first user body information;
   obtaining at least one first sensing signal sensed by a first sensing device worn by a first user; and
   comparing first sport posture data generated based upon the at least one first sensing signal with the selected first piece of the sport posture reference data, so as to determine whether a first sport posture of the first user is correct or not.

10. The adaptive sport posture sensing method according to claim 9, further comprising, in a learning mode, the steps of:
    recording the first sport name, the first wearing position and the first user body information;
    obtaining at least one training signal sensed by the first sensing device; and
    establishing, according to the at least one training signal, the first piece of the sport posture reference data corresponding to the first sport name, the first waring position and the first user body information.

11. The adaptive sport posture sensing method according to claim 9, further comprising, in the determination mode, the steps of:
    selecting a second piece among the multiple established pieces of the sport posture reference data according to a second sport name, a second wearing position and second user body information;
    obtaining at least one second sensing signal sensed by a second sensing device worn by a second user; and
    comparing second sport posture data generated based upon the at least one second sensing signal with the selected second piece of the sport posture reference data, so as to determine whether a second sport posture of the second user is correct or not.

12. The adaptive sport posture sensing method according to claim 9, wherein the first piece of the sport posture reference data is further selected according to a wearing manner.

13. The adaptive sport posture sensing method according to claim 9, wherein the first user body information comprises a height, a weight, a gender, an age and a health status of the first user.

\* \* \* \* \*